United States Patent [19]

Stoub

[11] Patent Number: 4,575,810

[45] Date of Patent: Mar. 11, 1986

[54] METHOD AND CIRCUIT FOR PROCESSING PULSES BY APPLYING THE TECHNIQUE OF WEIGHTED ACQUISITION

[75] Inventor: Everett W. Stoub, Villa Park, Ill.

[73] Assignee: Siemens Gammasonics, Inc., Des Plaines, Ill.

[21] Appl. No.: 474,409

[22] Filed: Mar. 11, 1983

[51] Int. Cl.$^4$ .................. G06F 15/20; G01T 1/20
[52] U.S. Cl. .................. 364/581; 364/527; 250/363 R; 250/369
[58] Field of Search ........... 364/581, 571, 527, 516, 364/414, 518; 250/363 R, 363 S, 369

[56] References Cited

U.S. PATENT DOCUMENTS

| | | |
|---|---|---|
| 3,011,057 | 11/1961 | Anger . |
| 4,029,948 | 6/1977 | Hounsfield .................. 364/581 X |
| 4,117,538 | 9/1978 | Shrader et al. ............... 364/581 X |
| 4,136,314 | 1/1979 | Blackmer et al. ............ 364/581 X |
| 4,298,944 | 11/1981 | Stoub et al. . |
| 4,316,257 | 2/1982 | DelMedico et al. . |
| 4,323,977 | 4/1982 | Arseneau . |

OTHER PUBLICATIONS

Journal of Nuclear Medicine, vol. 12, No. 11, Nov. 1971, pp. 703–706.
Journal of Nuclear Medicine, vol. 12, No. 10, Oct. 1971, pp. 690–696.
Journal of Nuclear Medicine, vol. 16, No. 1, Jan. 1975, pp. 102–104.
Journal of Nuclear Medicine, vol. 14, No. 2, Feb. 1973, pp. 67–72.
"Aspects of Imaging and Counting in Nuclear Medicine Using Scintillation and Semiconductor Detectors", by R. N. Beck et al., presented at the 13th Scintillation and Semiconductor Counter Symposium, Mar. 1–3, 1972, in Washington, DC.
Reprint IAEA-SM-164/301 from "Medical Radioisotopes Scintigraphy 1972", vol. 1, pp. 3–45.
Siemens brochure Micro Dot Imager, Model 3132, RR88010M509.
Siemens brochure Scintiview II, RR118010M529.

Primary Examiner—Edward J. Wise
Attorney, Agent, or Firm—Mark H. Jay

[57] ABSTRACT

A method and a circuit are provided for processing pulses, caused by a radioactive source and produced by an imaging radiation detector, by applying the technique of weighted acquisition for forming an image. An image weight function is formed corresponding to the source radiation, said function being dependent on the energy of said pulses in consideration of both the energy dependent signal-to-noise ratios of said pulses and the energy dependent modulation transfer functions of said pulses. Thereby a weighting pulse is obtained for each of said pulses, the particular value of said weighting pulse determined by the observed energy of said pulse. Said weighting pulses are then accumulated as said image.

14 Claims, 10 Drawing Figures

METHOD AND CIRCUIT FOR PROCESSING PULSES BY APPLYING THE TECHNIQUE OF WEIGHTED ACQUISITION

BACKGROUND OF THE INVENTION

1. Field of the Invention

This invention relates to a method and a circuit for processing pulses by applying the technique of weighted acquisition for forming an image. The pulses are particularly caused by a radioactive source and produced by an imaging radiation detector, such as a scintillation camera for detecting gamma rays.

2. Description of the Prior Art

Radiation detectors are widely used as diagnostic tools for analyzing the distribution of a radiation-emitting substance in an object under study, such as for the nuclear medical diagnosis of a human body organ. A typical radiation detector of a type to which the present invention relates is a commercial version of the Anger-type scintillation camera, the basic principles of which are described in Anger U.S. Pat. No. 3,011,057.

Such a scintillation camera can take a "picture" of the distribution of radioactivity throughout an object under investigation, such as an organ of the human body which has taken up a diagnostic quantity of a radioactive isotope. As individual gamma rays are emitted from the distributed radioactivity in the object and pass through a collimator, they produce scintillation events in a thin planar scintillation crystal. The events are detected by photodetectors positioned behind the crystal.

Electronic circuitry translates the outputs of the photodetectors into X and Y coordinate signals which indicate the position in the crystal of each event and a Z signal which indicates generally the energy of the event and is used to determine whether the event falls within a preselected energy range (window). A picture of the radioactivity distribution in the object may be obtained by coupling the X and Y signals which fall within the preselected energy window to a display, such as a cathode ray oscilloscope which displays the individual scintillation events as spots positioned in accordance with the coordinate signals. The detection circuitry typically provides for integrating a large number of spots onto photographic film.

In modern scintillation cameras which comprise circuitry for energy and linear spatial distortion correction, such as described in Stoub et al. U.S. Pat. No. 4,298,944, Del Medico et al. U.S. Pat. No. 4,316,257 or Arseneau U.S. Pat. No. 4,323,977 for example, the Z signal is tested against a set of three energy signal windows (single channel analyzer) which are pre-set according to the isotope being imaged. Thus events having Z signals within any window are included as counts in the image, while all other events are excluded. The ultimate purpose of this test is two-fold: (1) to include primary, (photopeak) events in the image and (2) to exclude scattered gamma ray and fluorescent X-ray events from the image. The capability of scintillation cameras for making this window test has been decisive for nuclear medical imaging. Image intensifier cameras with outstanding spatial resolution, but without any capability for this test, have all been notable failures in nuclear radiography.

However, even scintillation cameras which comprise circuitry for linear energy and spatial distortion correction, are not able to perfectly accept all photopeak events and reject all others. This fact is traceable to the very nature of scattering and to the finite energy resolution of the camera scintillator. Normally each scintillation camera has only a finite resolution, which blurs both photopeak and scatter. As the amount of scatter material increases, or as the depth of the gamma source increases, the relative proportion of scatter events in the image also increases. The inclusion of scatter events in addition to non-scatter events in an image degrades lesion visibility, image contrast and system resolution.

One method, as a former attempt of reducing the scatter photon contribution to the events measured under the photopeak, is to raise the baseline of the Pulse Height Analyzer. But this necessarily results in a lower sensitivity because some primary photons are excluded when the baseline raises.

Another method, as an attempt of reducing the scatter influence, is the so called "window shifting". This means that for each used isotope a specific window is determined which is supposed to be the "best one" with regard to photopeak-to-scatter ratio. But this method, which for example is described in a study entitled "Optimizing the Window of an Anger Camera for $^{99m}Tc$" by Theodore P. Sander et al., Journal of Nuclear Medicine, Vol. 12, No. 11, November 1971, 703–706, or in a study entitled "Effect of Pulse-Height Selection on Lesion Detection Performance" by F. D. Roll o et al., Journal of Nuclear Medicine, Vol. 12, No. 10, October 1971, 690–696, is also not satisfying.

A further method as an attempt of reducing the scatter influence is the so called "method of scatter subtraction". To compensate for the magnitude of scatter two windows are set, a first window for the photopeak together with scatter and the second window for scatter alone. The answer of the second window is then subtracted from the answer of the first window. But this scatter subtraction method which is for example described in a study entitled "Effects of Scatter Subtraction on Image Contrast" by Francis B. Atkins et al., Journal of Nuclear Medicine, Vol. 16, No. 1, January 1975, 102–104, or in a study entitled "Reduction of the Effects of Scattered Radiation on a Sodium Iodide Imaging System" by Peter Bloch et al., Journal of Nuclear Medicine, Vol. 14, No. 2, February 1973, 67–72, is also not satisfying.

A more successful method of reducing the scatter influence could have been the "method of weighted acquisition", which method is for example described in a paper entitled "Aspects of Imaging and Counting in Nuclear Medicine Using Scintillation and Semiconductor Detectors", by R. N. Beck et al., which paper was presented at the 13th Scintillation and Semiconductor Counter Symposium, Mar. 1–3, 1972, in Washington, DC. Another study discussing the "method" of weighted acquisition" is "Advances in Fundamental Aspects of Imaging Systems and Techniques", by R. N. Beck et al., reprint IAEA-SM-164/301 from "Medical Radioisotopes Scintigraphy 1972" Vol. 1, pages 3–45, especially pages 29, 30, 44 and 45.

But, the "method of weighted acquisition" was never brought to practical implementation. This may have been due to the fact, that this method was not well done in the prior art such that a reduction to practice was impossible till today.

SUMMARY OF THE INVENTION

It is an object of the present invention to provide an improved method and circuit for processing pulses by applying the technique of weighted acquisition in order to reduce or eliminate scatter.

It is a further object of the present invention to provide an improved weighted acquisition technique for processing pulses, which uses all of the energy spectrum data received by a radiation camera, such as a scintillation camera.

It is another object of the present invention to provide an improved weighted acquisition technique for processing pulses produced by a radiation camera, such as a scintillation camera with substantial benefits to clinical image quality, and with modest costs for implementation and production.

Briefly and in accordance with one embodiment of the invention, a method and circuit is provided for processing pulses, caused by a radioactive source and produced by an imaging radiation detector, by applying the technique of weighted acquisition for forming an image, wherein an image weight function corresponding to the source radiation is formed, said function being dependent on the energy of said pulses in consideration of both the energy dependent signal-to-noise ratios of said pulses and the energy dependent modulation transfer functions of said pulses, and wherein a weighting pulse for each of said pulses is obtained, the particular value of said weighting pulse determined by the observed energy of said pulse, and wherein said weighting pulses are accumulated as said image.

According to the present invention an image weight function is formed which is dependent on the energy of the pulses to be processed in consideration of both the energy dependent signal-to-noise ratios of the pulses and the energy dependent modulation transfer functions of said pulses. In prior art an image weight function is formed being dependent on the energy of said pulses in consideration of the energy dependent signal-to-noise ratio solely. In consideration of both signal-to-noise ratio and modulation transfer function an improved weighted acquisition technique for processing pulses is provided which eliminates scatter without degrading the signal-to-noise ratio. With regard to radiation cameras, such as scintillation cameras, thus an improved weighted acquisition technique for processing pulses produced by such a camera is provided, with substantial benefits to clinical image quality, and with modest costs for implementation and production.

There have been outlined rather broadly the more important objects, features and advantages of the invention in order that the detailed description thereof that follows may be better understood, and in order that the present contribution to the art may be better appreciated. There are, of course, additional features of the invention that will be described more fully hereinafter. Those skilled in the art will appreciate that the conception on which this disclosure is based may readily be utilized as the basis for the designing of other arrangements for carrying out the purposes of this invention. It is important, therefore, that this disclosure be regarded as including such equivalent arrangements as do not depart from the spirit and scope of the invention.

BRIEF DESCRIPTION OF THE DRAWINGS

An embodiment of the invention has been chosen for purposes of illustration and description, and is shown in the accompanying drawings forming a part of the specification, wherein.

DESCRIPTION OF THE PREFERRED EMBODIMENT

Figure 1:
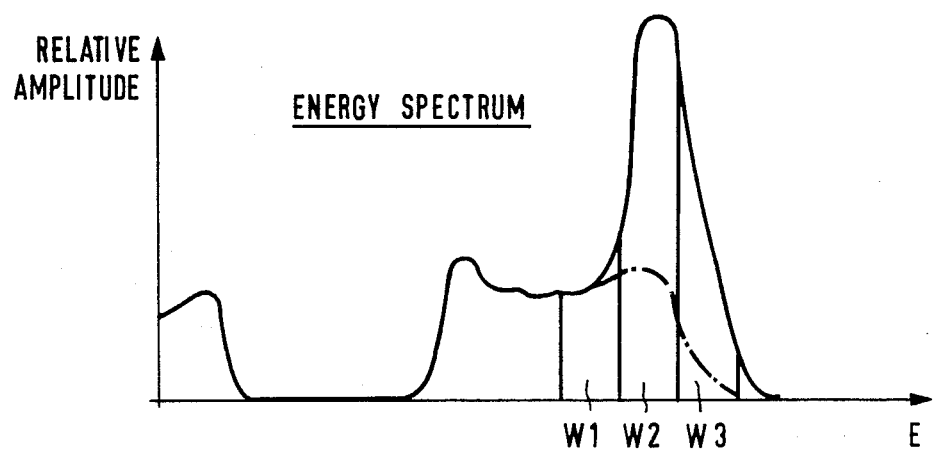
FIG. 1 shows a simplified illustration of a three-channel weighted acquisition concept for image enhancement for merely explaining the principle of the technique of weighted acquisition.
Figure 2:
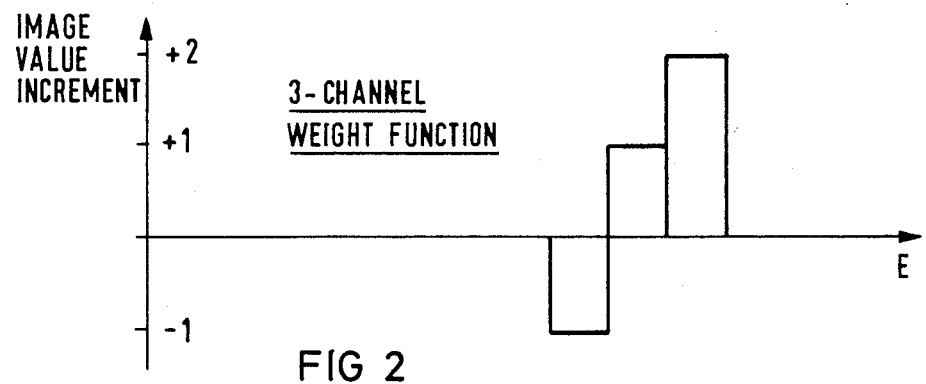
FIG. 2 shows a fictitious weight function corresponding to the three-channel method of FIG. 1.

As a completely synthetic example to illustrate the concept of weighted acquisition, consider the spectrum of FIG. 1. Suppose that events in the upper section of the photopeak were known to provide twice a much image information as those in the lower section, and that events in a region just below the photopeak could be subtracted to remove scatter. One could set three special windows W1, W2, W3 (below, lower part, and upper part), acquire three images each corresponding to one each of the special windows and combine the images, as shown in FIG. 2, by adding the upper window image in twice, the lower once, and subtracting the below range window image. The result, with respect to conventional signal window imaging, would be a noticeable improvement in scatter rejection and a measurable improvement in resolution. However, it is likely that signal-to-noise ratios in the weighted image would not be larger than normal images, due to the simplistic nature of this synthetic example.

Figure 3:
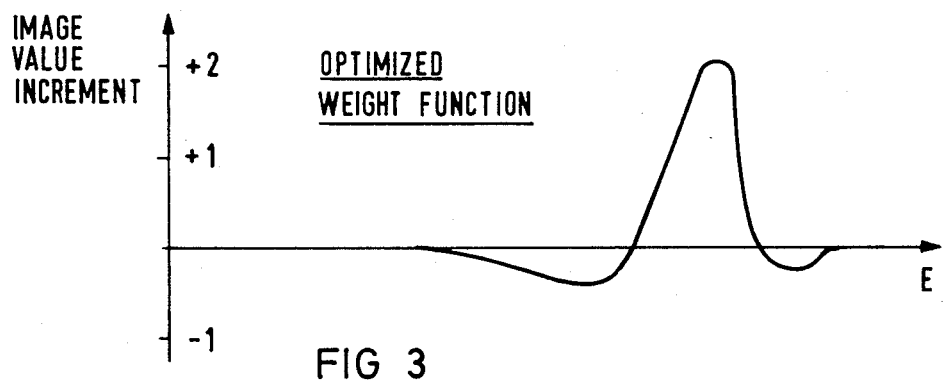
FIG. 3 shows a possible example for an optimized weight function using the entire energy spectrum for cancellation of most scatter contribution and enhancement of modulation transfer function values according to the invention.

A better result however can be reached by using carefully constructed weighting functions (for example corresponding to that one of FIG. 3) through improved signal-to-noise ratios and enhanced modulation transfer functions (MTF).

In the following, a method and a circuit is described how to develop a suitable weighting function and how to considerably improve image quality by using such a suitable weighting function for processing pulses caused by a radioactive source and produced by a scintillation camera for forming an image. As previously mentioned, events detected by the gamma camera are represented by three coordinates, X, Y, Z, the first two being position coordinates in the detector plane and the latter being the intensity of the scintillation flash, which is proportional to the gamma radiation energy converted in detection. The response of the camera to, say, a line source of activity placed above the collimated camera and parallel to the Y coordinate axis can be characterized by two density profiles, one along the X-coordinate axis, the other along the Z coordinate axis (a profile for Y could also be presented but, for this discussion, would be unremarkable). The X-coordinate profile is called a line source response function, LSRF, and the Z profile, an energy spectrum. The profiles are not independent: if only a narrow band of Z signal's used to accumulate a LSRF, rather dramatic changes are evidenced as the Z signal band is moved through the total range of Z. Likewise, a narrow band of X signal, gating the energy spectrum, yields significant changes in energy spectrum features.

The arithmetic process of extracting a signal S superimposed over a background B from the total response S+B yields a noise N (standard deviation) of $$\sqrt{S + 2B} .$$

If the LSRF is partitioned by a sequence of narrow contiguous Z bands, or channels, identified by an index i, the net LSRF due to any linear combinations of individual partitioned responses $LSRF_i$ is given by a sum over all channels:

$$LSRF(x) = \Sigma w_i \cdot LSRF_i(x), \quad (1)$$

where the $w_i$ are the linear combination factors, or weighting factors. Note that the use of normal, energy windows can be expressed using $w_i$ values of 1 for Z channels within the windows and 0 elsewhere. Likewise, the net signal level is given by $$S = \Sigma w_i \cdot S_i, \quad (2)$$

and net noise by $$N = \sqrt{\Sigma w_i^2 \cdot N_i^2} , \quad (3)$$

where the $S_i$ and $N_i$ correspond to the signal and noise values of the $LSRF_i$. Here is is assumed that signal adds linearly and noise in quadrature (without cross terms).

The LSRF (x) can be analyzed by inspection of its corresponding modulation transfer function MTF(f), a function of spatial frequency, f. The MTF value at a particular frequency expresses the relative sinusoidal modulation transferred from sinusoidal object to image. A "perfect" LSRF(x) is an infinitely narrow spike called a "delta function", which corresponds to a perfect MTF(f) equal to unity at all frequencies. Practical MTF(f) performance falls below unity above some frequency; typically only the DC term (zero frequency) has unit value.

The factors S, N, and MTF may be combined to form a reliable figure-of-merit Q for imaging particular object distributions. The simplest of these figures-of-merit is that for a sinusoidal object of spatial frequency $f_o$:

$$Q_s(f_o) = S \cdot MTF^2(f_o), \quad (4)$$

which has units of signal per unit area, per unit time. Thus, $Q_s$ represents the rate at which signal amplitude is accumulated, per unit area, for a sinusoidal object. For non-weighted systems, S might be interpreted directly as a Poisson statistic and could yield the image signal-to-noise ratio $$S/N = S/\sqrt{S} = \sqrt{S} \quad (5)$$

While this expression has some importance, the presence of scatter, fluorescent, and septal penetration components yields a synthetically high (optimistic) ratio. In the spirit of equation (4) this can be remedied by replacing S with the square of the signal-to-noise ratio:

$$Q_s(f_o) = (S/N)^2 \cdot MTF^2(f_o) \quad (6)$$

Finally, sinusoidal objects are infrequent subjects for gamma camera imaging. Often, the smallest lesions at the very limit of visibility in the image are being hunted. For this purpose, a figure-of-merit for imaging a point source, or delta function, is preferable. The ability to resolve a point source as an area of response in the image is proportional to the square of the integral of the MTF over the full frequency range of the measurement. In particular, a digital representation, with finite range, of an LSRF will yield a digital representation, also with finite range, of the MTF. Thus the integral is estimated by the sum of MTF values from zero frequency up to the maximum measured frequency response. Combining these ideas, the delta function figure-of-merit $Q_\delta$ can be expressed as $$Q_\delta = (S/N)^2 \cdot \left( \Sigma_f MTF(f) \right)^2 \quad (7)$$

This quantity represents the speed of the system in obtaining a detectable response to compact sources of activity.

Optimal weighted acquisition concerns the selection of weighting coefficients which yield the highest possible performance under some particular performance goal. Previous efforts at weighted acquisition focussed on signal-to-noise ratio exclusively, a focus that resulted in a distinctive loss of resolution and point source detectability. For the present invention, a more demanding goal is set, namely to optimize the delta function figure-of-merit itself. This path achieves a flexible balance between smooth (less noisy) images and crispness (resolution) improvements. To obtain these coefficients for optimal weighting, partial derivatives of $Q_\delta$ are evaluated for each weighting coefficient $w_i$; at the optimal levels for the $w_i$, all the partial derivatives are zero. Thus $$\frac{\partial Q_\delta}{\partial w_i} = 0, \text{ for all } w_i \quad (8)$$

The algebraic expressions (2) and (3) allow explicit expression for $\partial S/\partial w_i$ and $\partial N/\partial w_i$ terms. The $\partial \Sigma MTF/\partial w_i$ term is more tractable by finite difference ratios with computer evaluation. The expression derived for $w_i$ by equations (8) is $$w_i = \frac{(S_i/S) + K \cdot (\{\partial \Sigma MTF/\partial w_i\}/\Sigma MTF)}{(N_i^2/N^2)} \quad (9)$$

where K is a scale factor introduced to emphasize the role of resolution in the performance of the $w_i$. Due to the inseparable nature of (9), the set of $w_i$ is found by a successive approximation method which seems to converge rapidly, only two or three iterations, on a stable solution.

Figure 4A:
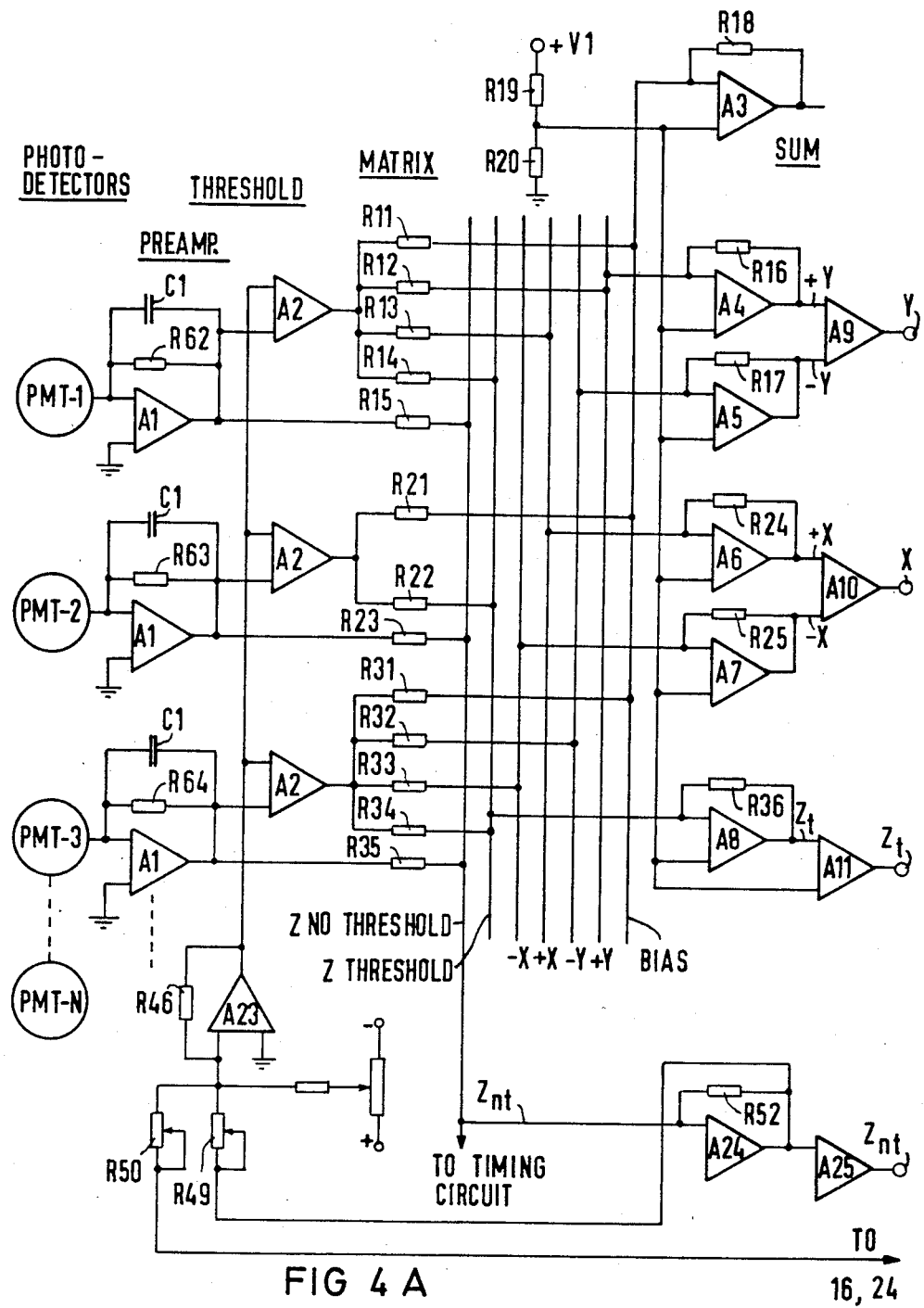
FIG. 4A–4C is a block circuit diagram of the most important components of a scintillation camera comprising a circuit for applying the technique of weighted acquisition according to the invention.

With reference to FIG. 4A, an Anger-type scintillation camera has a plurality of photomultiplier tubes PM-1 through PM-N (typically N=37 or 75 tubes mounted in a hexagonal array behind a scintillation crystal) which function together to detect a scintillation event that occurs when a gamma ray impinges on the scintillation crystal (the tubes PM-1 through PM-N are labeled "PHOTODETECTORS" in FIG. 1). For purposes of simplification only the circuitry associated with the first three photomultiplier tubes PM-1, PM-2, and PM-3 is illustrated in detail in FIG. 1.

The outputs of the photomultiplier tubes PM-1 through PM-N are separately coupled to respectively corresponding preamplifier circuits A1 ("PREAMP"). Each preamplifier circuit A1 has an output coupled to a separate threshold amplifier circuit A2 ("THRESHOLD"). Each of the threshold amplifiers A2 subtracts a prerequisite threshold voltage from the output of the particular preamplifier A1 with which it is associated. An amplifier A23 with a feedback loop employing a resistor R46 supplies a threshold bias to the threshold amplifiers A2. The threshold voltage is established as a function of the energy of the incoming scintillation event.

The threshold amplifiers A2 operate to pass the preamplifier A1 output signals to a resistor matrix ("MATRIX") and summing amplifiers A4 through A8 ("SUM") whenever the output signal from the corresponding preamplifier A1 exceeds the value of the threshold voltage. If the output of any of the respective preamplifiers A1 is below the threshold, the output signal of the corresponding threshold amplifier A2 is substantially zero. From the threshold preamplifier A1 outputs, the resistor matrix and summing amplifiers A4 through A8 develop positional coordinate output signals $+Y$, $-Y$, $+X$, $-X$, and a thresholded energy signal $Z_t$. The $+Y$, $-Y$, output signals are fed to a differential amplifier A9 where the $+Y$ and $-Y$ signals are consolidated into a single event Y positional coordinte signal. Similarly, the differential amplifier A10 develops a single consolidated X positional coordinate signal. The $Z_t$ signal passes through the amplifier A11.

The preamplifiers A1 also have outputs, connected through resistors R15, R23 and R35 directly to a "Z NO THRESHOLD" signal line of the resistor matrix, that are summed to provide an unthresholded energy signal $Z_{nt}$ which represents the total energy of the scintillation event.

According to FIG., 4B, the signals Y, X, $Z_t$, $Z_{nt}$ at the outputs of the amplifiers A9, A10, A11, A25 are each fed to an appropriate integrator circuitry 10, 12, 14, 16, each of which comprises two integrating amplifiers A30 with an integrating capacitor C2. The outgoing integrated signals $Y_I$, $X_I$, $Z_{tI}$ and $Z_{ntI}$ of the integrator circuitries 10, 12, 14, 16 serve as respective inputs to sample and hold circuitries 18, 20, 22 and 24. The outputs of the sample and hold circuitries 18, 20 and 22 are connected to the inputs of a first and second ratio computation circuitry 26 and 28.

The first ratio computation circuitry 26 forms a ratio signal $Y_I/Z_{tI}$ from the signals $Y_I$ and $Z_{tI}$. The second ratio computation circuitry 28 forms a ratio signal $X_I/Z_{tI}$ from the signals $X_I$ and $Z_{tI}$. The outputs of the ratio computation circuitries 26, 28 are fed to sample and hold circuitries 30 and 32. The output of the sample and hold circuitry 24 is transferred to a sample and hold circuitry 34. Each of the sample and hold circuitries 18, 20, 22, 24, 30, 32, 34 is triggered by a first pulse higher analyzer 36 at succeeding times.

The first pulse height analyzer 36 is controlled by the output signal of an amplifier A38, the inputs of which are connected to the input and the output of the integrator circuitry 16 for the $Z_{nt}$ signal. When an integration of the integrator circuitry 16 has been finished, i.e. when a $Z_{ntI}$ signal has fully developed, the pulse height analyzer 36 produces a first trigger signal on dotted line 40 which first trigger signal triggers the sample and hold circuitries 18, 20, 22 and 24 simultaneously to sample and hold the actual values of the $Y_I$, $X_I$, $Z_{tI}$ and $Z_{ntI}$ signal. After a specific time period, i.e. the time the ratio computation circuits 26 and 28 need for forming the ratio signals $Y_I/Z_{tI}$ and $X_I/Z_{tI}$, the pulse height analyzer 36 produces a second trigger signal on dotted line 42 which triggers the sample and hold circuitries 30, 32 and 34 simultaneously to sample and hold the actual output values of the ratio computation circuits 26, 28 on the one hand and the output value of the sample and hold circuitry 24 on the other hand.

The pulse height analyzer 36 also triggers a second pulse height analyzer 44 over a dotted line 45. The second pulse height analyzer 44 works as an energy analyzer which determines whether the energy of an energy corrected signal $Z_c$ falls within a preselected window (i.e. whether a signal is "valid").

The energy corrected signal $Z_c$ is produced by an on-line energy correction circuit as described in the Arseneau U.S. Pat. No. 4,323,977 for example, this on-line energy correction circuit comprises an analog-to-digital converter 46 for the output signal $Y_a$ of the sample and hold circuitry 30 and an analog to digital converter 48 for the output signal $X_a$ of the sample and hold circuitry 32. It further comprises a Z correction factor memory 50, and an energy signal modification circuitry 52 and a first mixer 54.

The energy corrected signal $Z_c$ is passed to the pulse height analyzer 44 on the one hand and a sample and hold circuitry 56 on the other hand. When the energy falls within the energy window of the pulse height analyzer 44, i.e. when the detected event which the Z-coordinate signal $Z_c$ is derived from is valid the pulse height analyzer 44 triggers the sample and hold circuitry 56 via dotted line 58.

The actual value of the $Z_c$ signal is thus shifted to the sample and hold circuitry 56. Besides triggering the sample and hold circuitry 56 the pulse height analyzer also triggers two further sample and hold circuitries 60 and 62. Due to this the actual value of the signal $Y_a$ is shifted to the sample and hold circuit 60 and the actual value of the signal $X_a$ is shifted to the sample and hold circuit 62 simultaneously when the actual value of the signal $Z_c$ is shifted to the sample and hold circuitry 56.

The pulse height analyzer 44 also produces a delayed logic signal $U_B$ on line 63. This delayed logic signal $U_B$ is applied as start pulse to a control logic circuitry, which is part of the circuit for weighted acquisition, as is later described in more detail.

The output of the sample and hold circuitry 60 is coupled to the first input of a second mixer 64, the second input of which is connected to a first output $\Delta Y$ of a spatial distortion correction circuitry. The output of the sample and hold circuitry 62 is connected to a first input of a third mixer 66. The second input of the third mixer 66 is connected to a second output $\Delta X$ of the spatial distortion correction circuitry.

The spatial distortion correction circuitry is also well-known in the art and for example described in the Arseneau U.S. Pat. No. 4,323,977. It comprises an analog-to-digital converter 68 for the signal $Y_a$ and an analog-to-digital converter 70 for the signal $X_a$. It further comprises a correction coefficient memory 72 and a correction interpolator 74 which can also comprise a distortion correction modification unit as described in Arseneau U.S. Pat. No. 4,323,977. The output signals $\Delta Y, \Delta X$ of the correction interpolator 74 are the outputs of the spatial distortion correction circuitry.

Figure 4B:
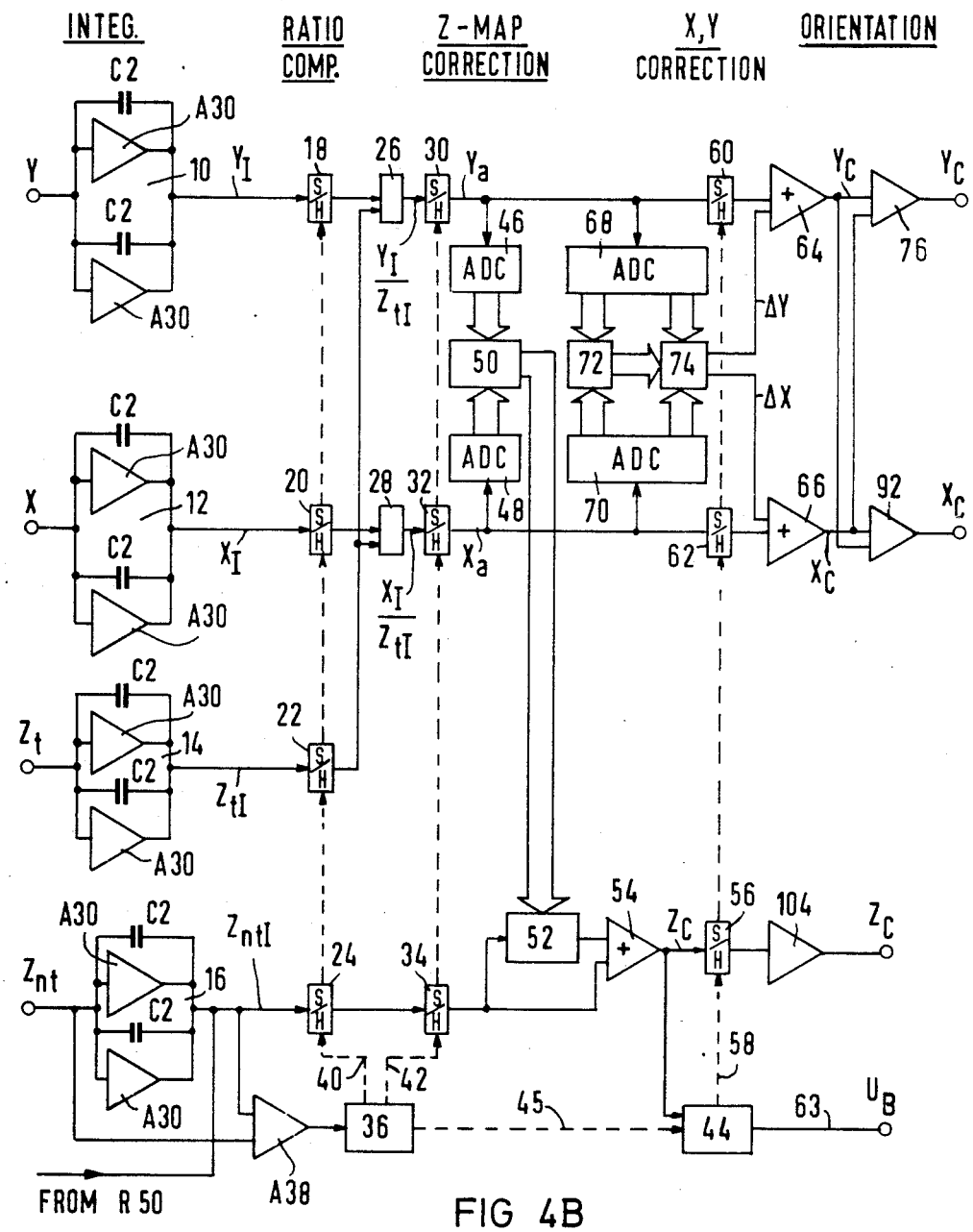
Figure 4C:
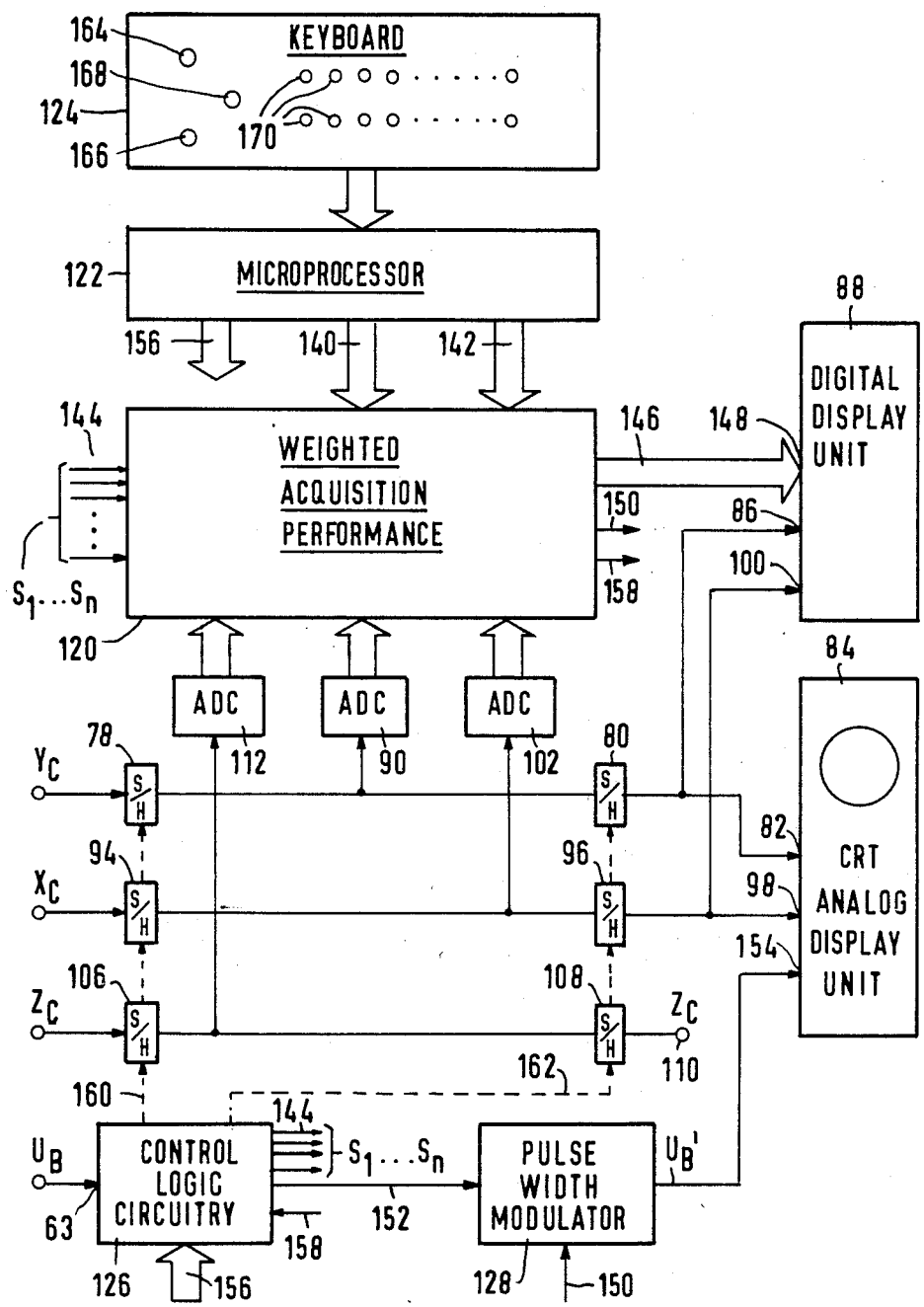

The mixers 64 and 66 correct the signals $Y_a$ and $X_a$ with respect to the correction signals $\Delta Y$ and $\Delta X$. The corrected signal $Y_c$ is then applied by means of a vertical orientation amplifier 76 and according to FIG. 4C by means of two sample and hold circuitries 78 and 80 to the vertical input 82 of an analog display unit 84, such as a cathode ray oscilloscope, and/or to the vertical input 86 of a digital display unit 88. It is also applied to a $Y_c$ signal analog to digital converter 90, as shown in FIG. 4C.

Correspondingly the corrected signal $X_c$ is applied by means of a horizontal orientation amplifier 92 and two sample and hold circuitries 94, 96 to the horizontal input 98 of the analog display unit 84 and/or the horizontal input 100 of the digital display unit 88. It is also applied to a $X_c$ signal analog to digital converter 102, as shown in FIG. 4C.

The $Z_c$ signal at the output of the sample and hold circuitry 56 is applied by means of an amplifier 104 and two sample and hold circuitries 106, 108 to an output 110 (e.g. for connection with a further pulse height analyzer for spectrum studies). The $Z_c$ signal is also applied to a $Z_c$ signal analog to digital converter 112, as shown in FIG. 4C.

The analog to digital converters 90, 102 and 112 are part of the circuit for weighted acquisition according to the present invention. As shown in FIG. 4C this circuit for weighted acquisition comprises furthermore a circuitry 120 for weighted acquisition performance, a microprocessor 122, a keyboard 124, a control logic circuitry 126 and a pulse width modulator 128.

The circuitry 120 for weighted acquisition performance, which as later described in more detail with respect to FIG. 5 comprises a weight function memory and a subtract buffer image memory, stands in communication with the microprocessor 122 by means of data and address buses 140 and 142. The circuitry 120 is also connected with the control logic circuitry 126 by means of control lines 144 for control signals $S_i$ to $S_n$ produced by the control logic circuitry for controlling the circuitry 120 for weighted acquisition performance. Furthermore, the circuit 120 is connected by means of a data and address bus 146 with a data and address input 148 of the digital display unit 88 and it is also connected by means of a control line 150 with a pulse width modulator 128.

The pulse width modulator 128 is controlled by the control logic circuitry 126 via control line 152. It produces an unblank signal $U_B{}^1$, the width of which depending on the control signal on line 150. The unblank signal $U_B{}^1$ is used to unblank the cathode ray tube of the analog display unit via unblank input 154. The control logic circuitry 126 is, as mentioned above, controlled by the logic signal $U_B$ of the pulse height analyzer 44 (FIG. 4B) via line 63. It is also controlled by the microprocessor 122 via bus 156 and by the circuitry 120 for weighted acquisition performance via line 158. The control logic circuitry 126 also switches the sample and hold circuitries 78, 94, 106 via line 160 and the sample and hold switches 80, 96, 108 via line 162.

The microprocessor 122 is controlled by the keyboard 124. This keyboard comprises a start button 164 for starting an image display cycle, a stop button 166 for interrupting an image display cycle and a reset button 168 for resetting the active elements of the circuit for weighted acquisition. The keyboard furthermore comprises a board of selection buttons 170 for selecting, from user's side, the appropriate weighting coefficients sets.

Figure 5:
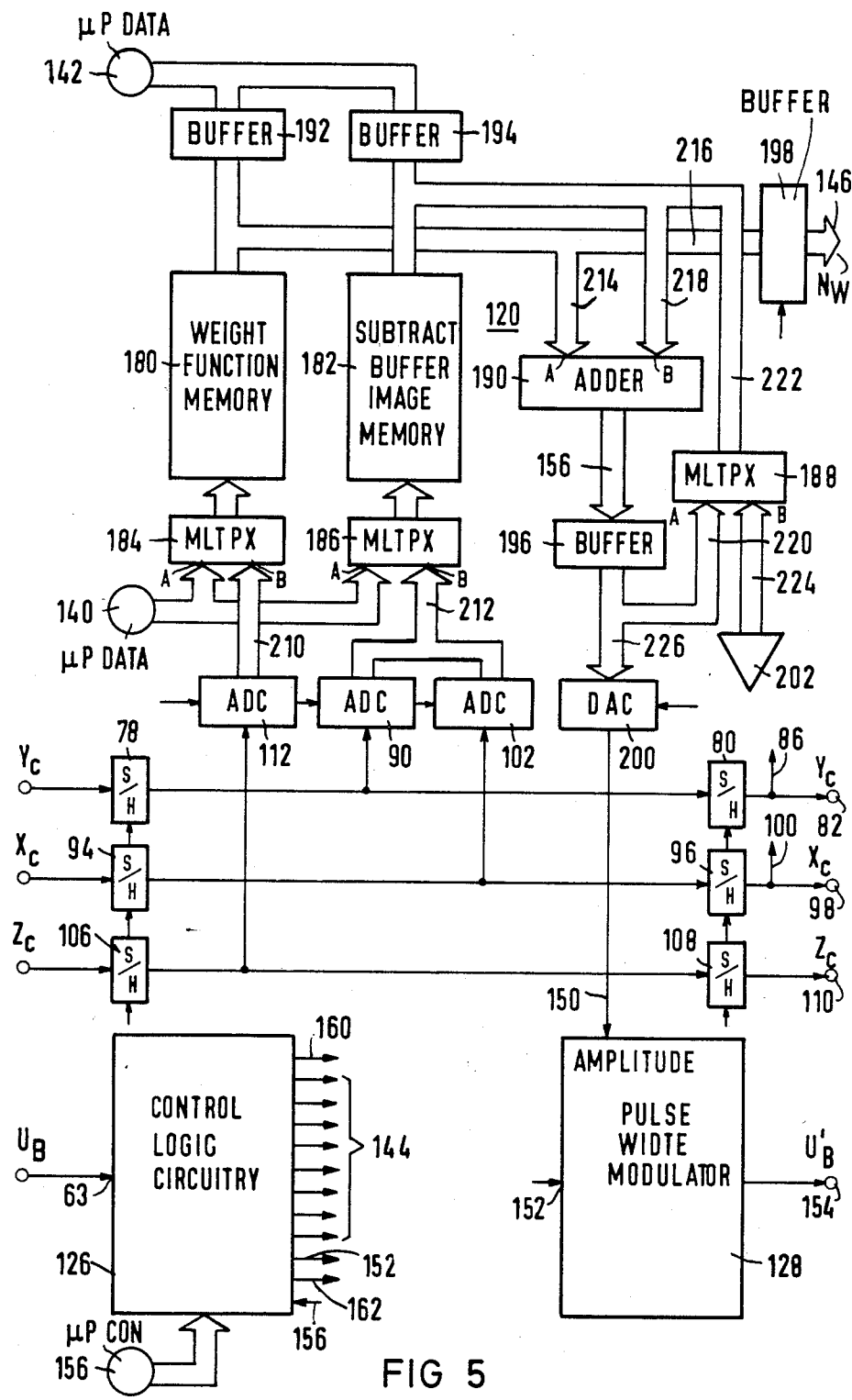
FIG. 5 is a more detailed schematic circuit diagram of the circuit for applying the technique of weighted acquisition according to the invention.

Referring now to FIG. 5, this figure shows a more detailed schematic circuit diagram of the circuit for applying the technique of weighted acquisition according to the present invention.

According to FIG. 5 the circuit for weighted acquisition performance 120 comprises a weight function memory 180 and a subtract buffer image memory 182 (e.g. both memories are RAMs). It also comprises multiplexer 184, 186 and 188, an adder 190, buffer 192, 194, 196 and 198, a digital to analog converter 200 and a zero pulse generator 202, which are connected to the weight function memory 180, the subtract buffer image memory 182, the microprocessor 122, the control logic circuitry 126, the pulse width modulator 128 and the analog to digital converters 90, 102 and 112 as shown in FIG. 5. The output of buffer 198 is connected via bus 146 to the input 148 of the digital display unit 88 and the output of the pulse width modulator 128 is connected with the unblank input 154 of the analog display unit 84 as shown in FIG. 4C.

The operation of the circuit for weighted acquisition is as follows:

(1) By pressing the buttons 170 of the keyboard 124 an appropriate weighting coefficient set is chosen;

(2) the multiplexer 184 is in position A and the buffer 192 is in a low resistance position. Thus the weight function memory 180 is able to receive from the microprocessor 122 data via buffer 192, and addresses via multiplexer 184 according to the selected weighting coefficient set;

(3) by pressing the reset button 168 of the keyboard 124, the subtract buffer image memory 182 is cleared;

(4) by pressing the start button 164 of the keyboard 124 a new study is started;

(5) each subsequent signal $U_B$ at the input of the control logic circuitry 126 then starts the processing as follows:

(a) a signal STSH1 for starting the first set of sample and hold circuitries 78, 94 and 106 is produced by the control logic circuitry 126 on line 160;

(b) the analog to digital converters 90, 102 and 112 are then started with signal STADC, produced by the control logic circuitry 126 to convert $Y_c$, $X_c$ and $Z_c$ at the outputs of the sample and hold circuitries 78, 94 and 106;

(c) the analog to digital converter 112 in response thereto produces an address for the weight function memory 180 via an address bus 210, which address passes through multiplexer 184, which has been set from A to B by signal WPWFM (write processor weight function memory) of the control and logic circuitry 126 to the weight function memory 180;

(d) the analog to digital converters 90 and 102 in response to the signal STADC produce addresses which are combined in address bus 212 and passed through multiplexer 186, which also has been set from A to B by a signal WPBIM (write buffer image memory) of the control and logic circuitry 126 to the subtract buffer memory 182;

(e) after addressing the weight function memory 180 information $N_w$ (weighting value for the event) leaves the memory and passes via bus 214 to the input A of the adder 190 and via bus 216 to the buffer 198;

(f) simultaneously with $N_w$ information $D_w$ (previous net accumulation of non positive coefficients of all previous events corresponding to the pixel location of the event selected by $X_c$ and $Y_c$) is passed from the subtract buffer image memory 182 to input B of the adder 190 via bus 218;

(g) the adder 190 performs the arithmetic sum $N_E = N_w + D_w$;

(h) a sign bit SIGNB is produced by the adder 190 on line 156, which for example is ZERO when $N_E > 0$ and ONE when $N_E \leq 0$;

(i) depending on the status of the sign bit SIGNB the control logic circuitry produces a signal SLNNE (select negative $N_E$), which sets the multiplexer 188 to A, when $N_E \leq 0$ and sets the multiplexer to B when $N_E > 0$;

(j) in position A of the multiplexer 188 the negative $N_E$ passes via bus 220 the multiplexer 188 and is applied via bus 222 to the subtract buffer image memory 182;

(k) in position B of the multiplexer 188 a ZERO from zero generator 202 passes via bus 224 the multiplexer 188 and is applied via bus 222 to the subtract buffer image memory 182;

(l) a signal WTBIM (write buffer image memory) is provided by the control logic circuitry 126 which signal causes the substract buffer image memory 182 to store the output information of multiplexer 188 delivered via bus 222;

(m) meanwhile buffer 196 has been switched by signal SLBNE (select buffer for signal $N_E$) to a low resistance value and $N_E$ passes the buffer 196 via bus 226 to the digital analog converter 200;

(n) a start signal STDAC for the digital to analog converter 200 is produced by the control logic circuitry 126 and the digital to analog converter 200 thus starts converting the output signal $N_E$ of the buffer 196 to produce positive or negative amplitude in direct proportion to the value $N_E$, which positive or negative amplitude is supplied to the pulse width modulator 128 via line 150;

(o) the pulse width modulator is started by a signal STPWM produced by the control logic circuitry 126 via line 152 after the conversion of $N_E$ by digital to analog converter 200 has been finished;

(p) in response to the starting signal STPWM the pulse width modulator 128 produces an unblank signal $U_B{}^1$ which has a minimum time length in the case of $N_E \leq 0$ and a greater time length for $N_E > 0$ in direct proportion to the value $N_E$;

(q) in the case of the signal $U_B'$ has minimum time length ($N_E \leq 0$) no exposure value is produced with respect to the analog display unit 84;

(r) in the case the signal $U_B'$ has greater time length ($N_E > 0$) an exposure value is produced which is linearly proportional to $N_E$;

(s) in this way the exposure index $N_E$ is reduced to account for scatter at the corresponding pixel location; by continuously storing the output of multiplexer 188 in the subtract buffer image memory 182 accurate account of scatter subtraction is maintained;

(t) the output $N_W$ of buffer 198 is applied to the digital display unit 88 via bus 146, when a signal SLBNW (select buffer for signal $N_W$) is produced by the control logic circuitry 126. Thus a digital display can be produced in addition to the analog display on the analog display unit 84 or separately thereto.

As a digital display unit, for example a Siemens SCINTIVIEW ™ display unit can be utilized, as it is for example described in the Siemens brochure SCINTIVIEW ™ II No RR 1180 10M529. In this case only a simple modification with respect to the digital memory has to be made. Normally in the digital memory of the SCINTIVIEW ™ the digit ONE is added to the selected pixel for the event. Instead, now the the signal $N_E$ via bus 146 has to be added.

As a analog display unit, for example a Siemens Micro Dot Imager ™ can be utilized as described, for example in the Siemens brochure Micro Dot Imager ™ Model 3132 Nr. RR88010M509. The same kind of modification has to be provided as described above for the SCINTIVIEW.

Figure 6:
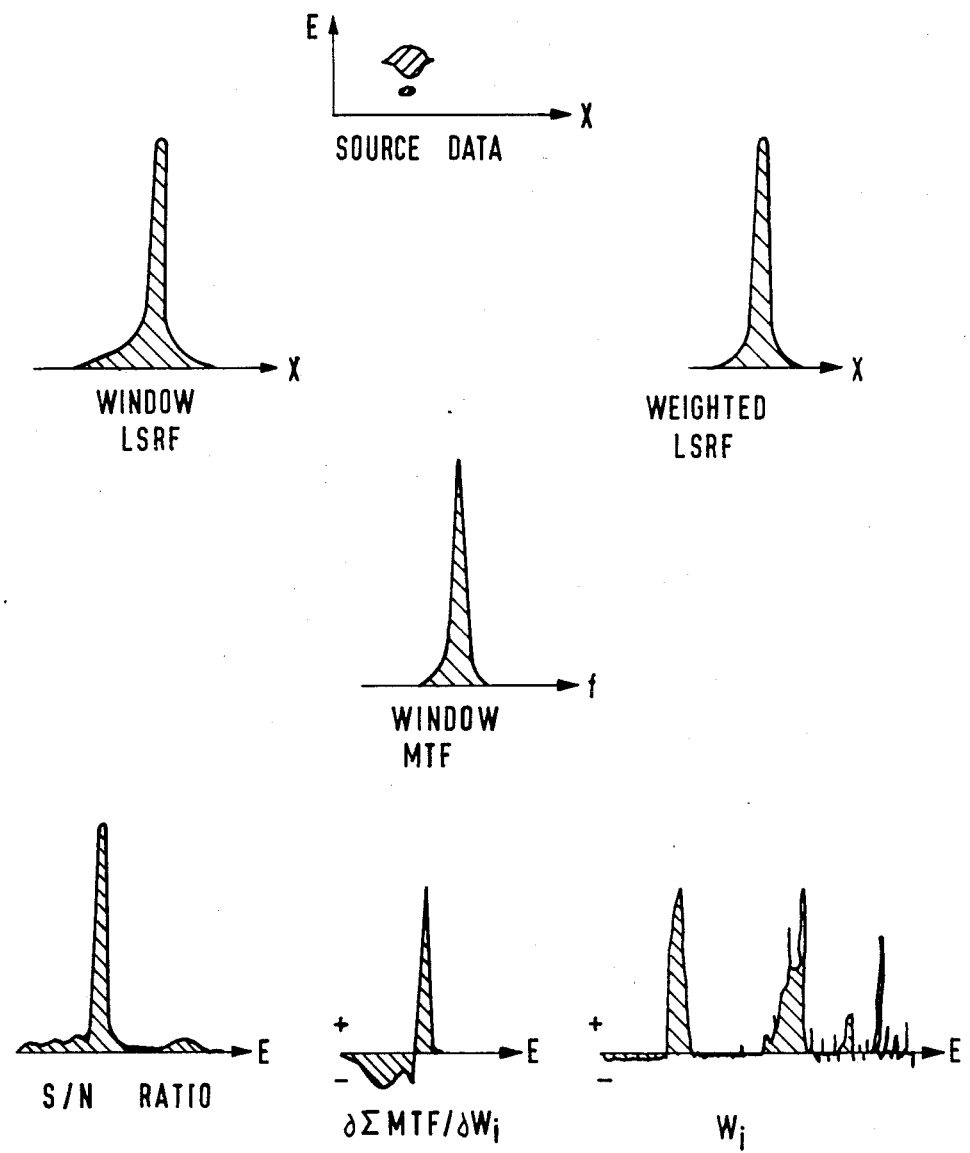
FIGS. 6 to 8 show with respect to three different isotopes ($^{99m}$Tc, $^{67}$Ga, and $^{201}$Tl, respectively) images of acquired data, profiles of LSRFA's, MTF's, intrinsic signal-to-noise ratio profiles, partial derivatives of the MTF integrals, and resulting weight function profiles.
Figure 7:
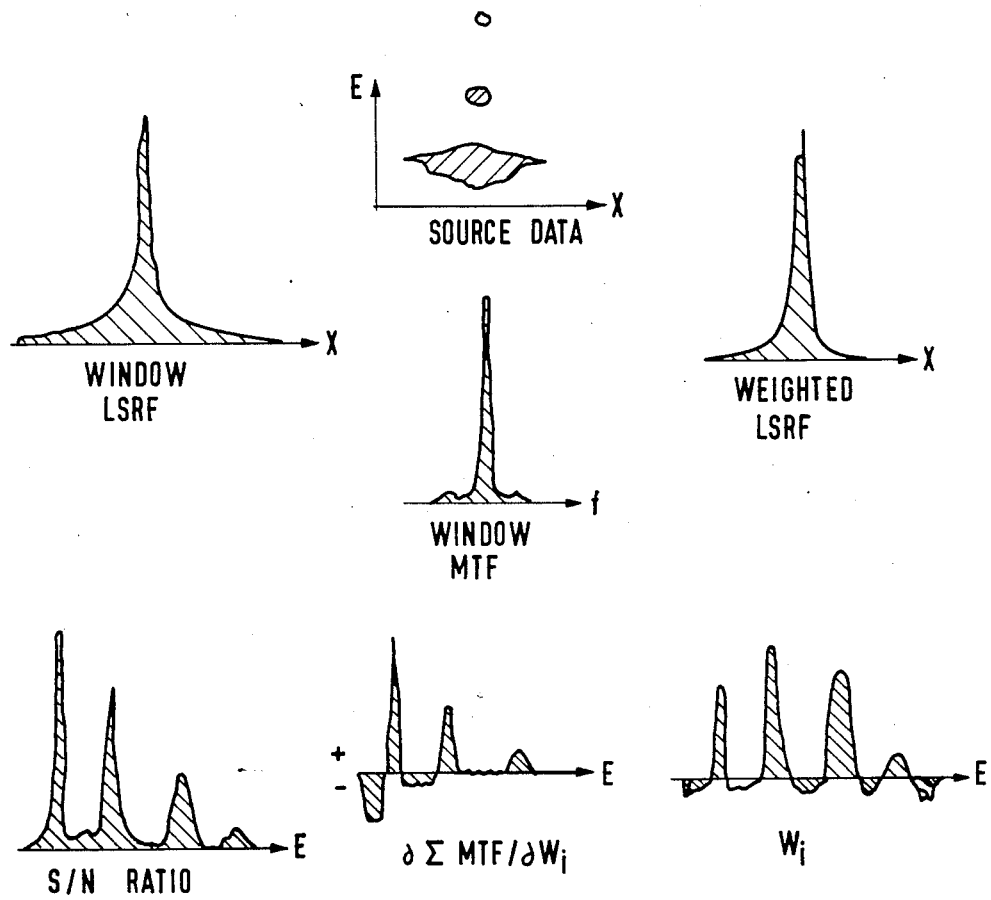
Figure 8:
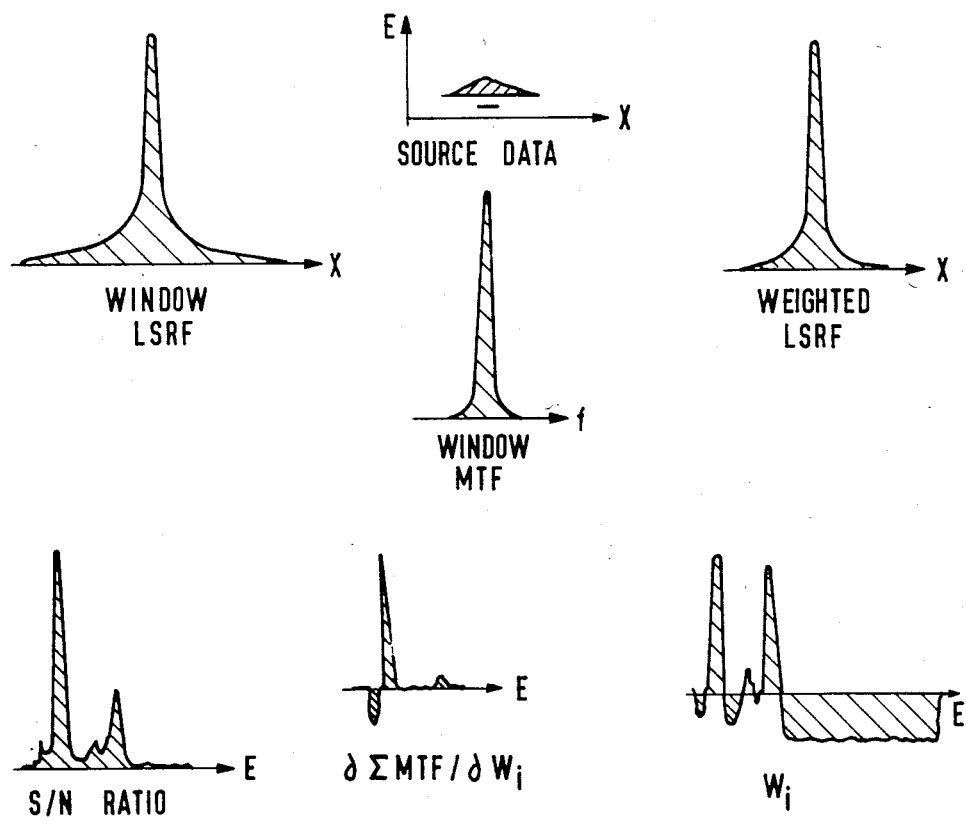

Referring now to FIGS. 6, 7 and 8. These figures give a good impression how advantageous the technique of weighted acquisition is when used according to the invention.

Three radioactive isotopes ($^{99m}$Tc, $^{67}$Ga, $^{201}$Tl) in common use have been analyzed for weighted acquisition enhancements. All results to date have centered on off-line recombination of LSRF profiles, obtained by the simple expedient of acquiring line source images with the Z signal replacing the redundant Y signal in the image memory addressing. These data have been extremely informative and suggestive of phenomena not readily predicted.

FIG. 6 shows $^{99m}$Tc source data, due to a line source at 10 cm in scatter, and the normal window LSRF, which are analyzed to yield the weighted LSRF using signal and noise spectra and partial derivatives of the MTF integral. The distribution of weighting coefficients illustrates the use of real-time scatter subtraction to improve the "tails" of the LSRF, as seen by comparison of normal and weighted LSRF plots.

FIG. 7 and 8 show corresponding images of acquired data profiles of LSRF's, MTF's, intrinsic signal-to-noise ratio profiles, partial derivatives of the MTF integrals, and resulting weight function profiles for $^{67}$Ga source data and $^{201}$Tl source data.

The following table lists the highlights of optimal weighted acquisition LSRF performance, signal-to-noise ratio, and figure-of-merit levels in comparison to standard "window" weighting function levels:

| CATEGORY | FUNCTION ratio = O/W % chng = $\frac{O - W}{W} \times 100\%$ | $^{99m}$Tc | SOURCE $^{67}$Ga | $^{201}$Tl |
|---|---|---|---|---|
| Figure-of-merit, $Q_8$ | ratio | 2.14 | 3.16 | 2.24 |
| Signal-to-noise, S/N | % chng | +16.50 | +13.80 | +1.80 |
| MTF integral, ΣMTF | % chng | +25.60 | +56.30 | +46.90 |
| LSRF: FWHM | ratio | 0.95 | 0.93 | 0.92 |
| LSRF: FWTM | ratio | 0.85 | 0.42 | 0.46 |

Note the 5% ($^{99m}$Tc) improvement in system line source response full width at half maximum (FWHM) performance: this could otherwise only be achieved by improving intrinsic resolution from 3.80 mm FWHM to about 2.34 mm, or, alternatively, by improving low energy all purpose (LEAP) collimator resolution from 7.75 mm to about 7.15 mm. The intrinsic resolution approach would require roughly three times the number of PMT's of the used gama camera. The collimator "improvement" would require a sensitivity reduction from 310 to about 265 counts per minute per microcurie of $^{99m}$Tc. Weighted acquisition yields this 5% resolution boost in system response with a sensitivity gain as well. System FWTM improvements are even more dramatic. All the indicators show substantial benefits. These benefits correlate with subjective assessment of image quality and with practical results in feature extraction and lesion detectability.

A general purpose weighting function table proposed for the weighted acquisition technique is shown in the following table.

| Function Block Number | Specific Radioisotope | Emitted Gamma Energies (keV) | Imaging Application |
|---|---|---|---|
| 0 | 99m$_{Tc}$ | 140, 143 | Bone, Liver, Lung Thyroid, Brain, Cardiovascular, Cisternography |
| 1 | 67$_{Ga}$ | 91, 93, 185, 209, 300, 394 | Tumor, Soft Tissue |
| 2 | 201$_{Tl}$ | 67–85, 135, 167 | Myocardium |
| 3 | 123$_I$ | 159, 440, 529 | Thyroid Liver |
| 4 | 131$_I$ | 80, 177, 284 364, 502 | Thyroid, Liver Lung |
| 5 | 111$_{In}$ | 172, 247 | Bone Marrow |
| 6 | 113m$_{In}$ | 392 | Brain, Liver, Lung |
| 7 | 197$_{Hg}$ | 66, 77, 191 | Kidney, Brain |
| 8 | 203$_{Hg}$ | 66, 279 | Kidney, Brain |
| 9 | 75$_{Se}$ | 66, 97, 121, 136 199, 265, 280 304, 401 | Pancreas |
| 10 | 133$_{Xe}$ | 81 | Lung ventilation |
| 11 | 51$_{Cr}$ | 302 | Spleen |
| 12 | (unit) | 48–560 (Z–ADC range) | (general) |
| 13 | 57$_{Co}$ | 122, 136 | Service, QA |
| 14 | 241$_{Am}$ | 60 | Service, QA |
| 15 | 133$_{Ba}$ | 53, 81, 160, 223 276, 303, 356 384 | Service, QA |

This table acommodates the major radioisotropes in present clinical use and allows acquisition for any source via keyboard 124.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims appended hereto. It will be appreciated that the selection, connection and layout of the various components of the described configurations may be varied to suit individual tastes and requirements.

What is claimed is:

1. A circuit for processing pulses caused by a radioactive source and produced by an imaging radiation detector by applying the technique of weighted acquisition for forming an image, said circuit comprising
   (a) a weight function memory having a data output;
   (b) a subtract buffer image memory having a data input and a data output;
   (c) an adder connected with the data output of said weight function memory and connected with said data output of said subtract buffer image memory for forming a sum signal of the output data of said weight function memory and said subtract buffer image memory;
   (d) means associated with said adder for producing a polarity signal in dependence on the polarity of said sum signal performed by said adder; and
   (e) means associated with said adder and controlled by said polarity signal for supplying a negative sum signal to the data input of said subtract buffer image memory.

2. A circuit according to claim 1, further comprising means associated with this adder and controlled by said polarity signal for applying a zero signal of a zero signal generator to said data input of said subtract buffer image memory, when the sum signal is positive.

3. A circuit according to claim 2, wherein said polarity signal is a sign bit which is in a first status when said sum signal is positive and which is in a second status when said sum signal is negative and wherein said means for supplying said negative sum signal and said means for supplying said zero signal comprising a multiplexer switchable dependent on the status of said sign bit into a first switching position, when the sign bit is in said second status and into a second switching position, when the sign bit is in said first status, whereby said multiplexer in said first switching position supplying said sum signal of said adder and in said second switching position supplying said zero signal of said zero signal generator to said data input of said subtract buffer image memory.

4. A circuit according to claim 3, wherein said sign bit is also in said second status when said sum signal is zero.

5. A circuit according to claim 3, wherein said sign bit is ZERO in said first status and ONE in said second status.

6. A circuit according to claim 1, further comprising
(a) a digital to analog converter receiving said sum signal of said adder as a digital input signal;
(b) a pulse width modulator connected to the analog output of said digital to analog converter; and
(c) an analog display unit having an unblank input connected with the output of said pulse width modulator;
wherein said pulse width modulator producing on its output an unblank signal for said analog display unit, which unblank signal has a minimum time length when the sum signal of said adder is negative, such that no exposure value is produced with respect to the analog display unit and which unblank signal has a greater time length when the sum signal of said adder is positive such that an exposure value is produced with respect to said analog display unit.

7. A circuit according to claim 6, wherein said unblank signal of said pulse width modulator has also said minimum time length, when the sum signal is zero.

8. A circuit according to claim 1, further comprising
(a) a keyboard for choosing an appropriate weighting coefficient set; and
(b) a microprocessor having an input connected with said keyboard and having a first data output and a first address output;
wherein said first data output is connected with the data input of said weight function memory and said first address output is connected with an address input of said weight function memory such that the weight function memory is able to receive data and addresses from said microprocessor according to the selected weighting coefficient set.

9. A circuit according to claim 8, further comprising
(a) a first address multiplexer having a first and a second address input and an address output; and
(b) a first analog to digital converter having an digital output and an analog input;
wherein the analog input of said first analog to digital converter is connected to an output for an Z energy signal of said imaging radiation detector and said digital output of said analog to digital converter is connected to the second address input of said first multiplexer and wherein said first address input of said first multiplexer is connected to said first address output of said microprocessor and the address output of said first multiplexer is connected to the address input of said weight function memory, such that in a first switching position of said first multiplexer said weight function memory is addressed by said microprocessor and in a second switching position said weight function memory is addressed by said first analog to digital converter.

10. A circuit according to claim 9, further comprising
(a) a second address multiplexer having a first and a second address input and an address output;
(b) a second analog to digital converter having a digital output and an analog input; and
(c) a third analog to digital converter having a digital output and an analog input;
wherein said analog input of said second analog to digital converter is connected to an X coordinate output and said analog input of said third analog to digital converter is connected to a Y coordinate output of said imaging radiation detector and said digital outputs of said second and third analog to digital converters are connected to the second input of said second multiplexer and wherein said first address input of said second multiplexer is connected to a second address output of said microprocessor and the address output of said second multiplexer is connected to the address input of said subtract buffer image memory, such that in a first switching position of said second multiplexer said subtract buffer image memory is addressed by said microprocessor and in a second switching position said subtract buffer image memory is addressed by said second and third analog to digital converters.

11. A circuit according to claim 10, wherein said microprocessor comprising a second data output, which is connected with said data input of said subtract buffer image memory.

12. A circuit according to claim 1, wherein said data output of said weight function memory is connected to a digital display unit.

13. A circuit for generating event counts for storage in an image accumulation memory to implement real-time area-weighted acquisition, comprising:
(a) a weight function memory for storing a weight function characteristic of a radioisotope to be used;
(b) an image buffer memory for storing residual weight function information accumulated during an exposure as a function of image location; and
(c) means for utilizing information read out of the weight function memory and the image buffer memory to determine an appropriate number of event counts which are to be added to the image accumulation memory to produce an area-weighted image.

14. The circuit of claim 13, wherein said means comprises:
(a) means for generating a non-integral number of event counts;
(b) means for rounding said non-integral number to an integral number of event counts which are to be added to the image accumulation memory;
(c) means for computing a difference between said integral and non-integral numbers; and
(d) means for adding said difference to the image buffer memory.

* * * * *